(12) United States Patent
Heinzel et al.

(10) Patent No.: US 8,992,826 B2
(45) Date of Patent: Mar. 31, 2015

(54) METHOD FOR PRODUCING A SEMIFINISHED PRODUCT AND SEMIFINISHED PRODUCT FOR ELECTRICAL CONTACTS AND CONTACT PIECE

(75) Inventors: Helmut Heinzel, Tiefenbronn (DE); Dirk Moog, Remchingen (DE); Norbert Witulski, Pforzheim (DE); Stefan Dasler, Pforzheim (DE); Andreas Kraus, Muehlacker (DE); Johann Wenz, Pforzheim (DE); Evelin Mahle-Moessner, Pforzheim (DE); Volker Behrens, Bretten (DE)

(73) Assignee: Doduco GmbH, Pforzheim (DE)

( * ) Notice: Subject to any disclaimer, the term of this patent is extended or adjusted under 35 U.S.C. 154(b) by 999 days.

(21) Appl. No.: 13/127,544

(22) PCT Filed: Oct. 27, 2009

(86) PCT No.: PCT/EP2009/007661
§ 371 (c)(1),
(2), (4) Date: Jun. 22, 2011

(87) PCT Pub. No.: WO2010/051922
PCT Pub. Date: May 14, 2010

(65) Prior Publication Data
US 2011/0262293 A1 Oct. 27, 2011

(30) Foreign Application Priority Data
Nov. 6, 2008 (DE) .......................... 10 2008 056 263

(51) Int. Cl.
B22F 7/06 (2006.01)
C22C 32/00 (2006.01)
A61L 27/20 (2006.01)
A61L 27/56 (2006.01)
A61L 27/58 (2006.01)

(52) U.S. Cl.
CPC ............. *C22C 32/0084* (2013.01); *A61L 27/20* (2013.01); *A61L 27/56* (2013.01); *A61L 27/58* (2013.01); *B22F 7/06* (2013.01); *B22F 2998/10* (2013.01); *B22F 2999/00* (2013.01); *C22C 32/0021* (2013.01)
USPC ........................................................... 419/5

(58) Field of Classification Search
CPC ................................ B22F 1/0088; B22F 3/04
USPC .............................................. 419/5, 8, 18, 19
See application file for complete search history.

(56) References Cited

U.S. PATENT DOCUMENTS

| 3,226,517 | A |   | 12/1965 | Schreiner |
|-----------|---|---|---------|-----------|
| 3,335,001 | A |   | 8/1967  | Drew et al. |
| 3,560,170 | A |   | 2/1971  | Duerrwaechter et al. |
| 3,864,827 | A | * | 2/1975  | Schreiner et al. ............... 29/875 |
| 4,243,413 | A | * | 1/1981  | Shibata ........................... 75/234 |
| 4,456,662 | A |   | 6/1984  | Malikowski et al. |
| 4,622,269 | A |   | 11/1986 | Leung et al. |
| 4,681,702 | A |   | 7/1987  | Schreiner et al. |
| 5,445,895 | A |   | 8/1995  | Behrens et al. |
| 5,846,655 | A |   | 12/1998 | Henning et al. |

FOREIGN PATENT DOCUMENTS

| DE | 32 12 005 C2 | 5/1986 |
| DE | 41 26 220 A1 | 2/1993 |
| DE | 32 12 005 A1 | 10/1993 |
| DE | 195 23 922 A1 | 10/1996 |
| EP | 0 299 099 A1 | 1/1989 |
| EP | 0 299 099 B1 | 1/1989 |
| GB | 991433 A | 5/1965 |

* cited by examiner

*Primary Examiner* — George Wyszomierski
*Assistant Examiner* — Ngoclan T Mai
(74) *Attorney, Agent, or Firm* — Hackler Daghighian & Martino

(57) ABSTRACT

The method relates to a method for producing a strand-like, particularly band-like semi-finished part for electrical contacts, wherein the semi-finished part has a top side intended for making the electrical contact, said top side made from a silver-based composite material in which one or multiple metal oxides or carbon are embedded, and has a carrier layer supporting the composite material made of easily solderable or weldable ignoble metal, and method having the following steps: Powder-metallurgic production of a block made from the silver-based composite material, encasing of the block made of the composite material with a powder made from the easily solderable or weldable ignoble metal, compressing the block, encased by the metal powder, to condense the metal powder, sintering the compressed block in a reducing atmosphere or in an inert atmosphere or in a vacuum, avoiding the formation of fluid eutectics from the silver of the composite material and from the non-precious metal with which the block made from the silver-based composite material is encased, reshaping of the sintered block by extrusion pressing, creating a partial strand with a top side made from composite material and a bottom side made from non-precious metal.

22 Claims, No Drawings

METHOD FOR PRODUCING A SEMIFINISHED PRODUCT AND SEMIFINISHED PRODUCT FOR ELECTRICAL CONTACTS AND CONTACT PIECE

The invention relates to a method for producing a semifinished product for electrical contacts, comprising an upper face made of a silver-based composite material intended for the electrical contact-making, one or more metal oxides or carbon being embedded in the composite material, and a carrier layer made of easy-to-solder or easy-to-weld metal, on which the composite material is located.

Silver-based composite materials comprising embedded metal oxide or carbon particles cannot be welded and soldered, or only with great difficulty. For this reason, when producing semifinished products for electrical contacts, a lower face of the contact material is provided with a carrier layer comprising easy-to-solder or easy-to-weld metal. While the silver carrier layers are relatively easy to apply to contact materials by plating of a silver strip, applying a weldable carrier layer comprising considerably less expensive copper or other base metals poses considerable problems. Contrary to silver, copper oxidizes very quickly when exposed to air, so that copper strips do not adhere, or adhere very poorly, to contact materials because of an oxide layer, even under the action of pressure and elevated temperatures.

From EP 0 299 099 B1, it is known to provide small contact plates made of a silver-based composite material in which metal oxide particles are embedded with a solderable or weldable carrier layer by pressing the small contact plates together with a metal foil or a metal powder layer at elevated temperatures under an inert gas atmosphere or a reducing atmosphere. The production of a semifinished product using a single pressing technique is also known from DE 32 12 005 C2, which discloses the production of a two-layer molding by pressing together a lower layer made of copper powder and an upper layer made of a composite powder comprising silver and metal oxide, and by subsequently sintering it in an inert atmosphere.

It is the object of the invention to show a way of how a strip-shaped semifinished product for electrical contacts can be produced cost-effectively, which comprises an upper face made of a silver-based composite material intended for electrical contact-making and a lower face made of easy-to-solder or easy-to-weld base metal.

This object is achieved by a method having the characteristics of claim 1. Advantageous refinements of the invention are the subject matter of the dependent claims.

In a method according to the invention, first a block comprising a silver-based composite material is produced using a powder-metallurgical process, for example by mixing silver powder with metal oxide powder, pressing it, and subsequently sintering it. It is also possible, for example, to mix silver powder with a base metal powder, press it, and subsequently sinter it in an oxidizing atmosphere, whereby metal oxide particles are produced by oxidation of the base metal particles.

In a second step, the powder-metallurgically produced block is covered with a powder made of an easy-to-solder or easy-to-weld base metal, which is intended to form the carrier layer in the finished semifinished product, and is subsequently isostatically pressed, preferably at pressures of 500 bar to 2500 bar. The base metal used to form the carrier layer can be nickel, iron or copper and alloys of these metals, with copper and copper-base alloys, in particular brass, being particularly preferred.

The preferably isostatically pressed block is sintered in a further production step under non-oxidizing conditions. The pressed block can thus be sintered, for example, in a reducing atmosphere, an inert atmosphere, or in a vacuum. Sintering is carried out preventing the formation of a liquid eutectic from the silver of the composite material and from the base metal, with which the block made of the silver-based composite material is covered.

The formation of a liquid eutectic can be prevented most easily by carrying out the sintering at a temperature that is lower than the eutectic formation temperature, which is to say, for example, at a temperature of less than 779° C. when using copper as the base metal, which is the formation temperature of the silver-copper eutectic. The formation of a liquid eutectic, however, can also be prevented by providing an intermediate layer acting as a diffusion barrier between the block comprising the composite material and the cover formed of the base metal powder. Such an intermediate layer can be formed in particular by wrapping the block made comprising composite material with a foil made of a material forming a diffusion barrier After wrapping the composite material block, the base metal powder may be provided around the wrapped block and bonded thereto by isostatic pressing. Notably intermediate layers made of iron, nickel or cobalt and alloys of these metals are suited as the diffusion barrier, with nickel and nickel alloys being particularly preferred. The intermediate layer acting as the diffusion barrier is preferably dimensioned so that it is at least 3 µm, in particular at least 5 µm, and preferably 10 µm to 50 µm thick in the finished semifinished product.

In a particularly preferred embodiment, sintering takes place first in a reducing atmosphere, notably in hydrogen, at a temperature of less than 700° C., and subsequently sintering takes place under an inert atmosphere, notably under nitrogen, or a vacuum at a higher temperature, preferably at least 750° C. In this way, during a first sintering step, under a reducing atmosphere, potentially present oxide layers of the grains of the base metal powder, for example, copper, can be reduced, without reducing the metal oxide particles, for example tin oxide or zinc oxide particles, of the composite material. In a second sintering step under an inert atmosphere or under a vacuum, the sintering temperature can be raised, so that the grains of the metal powder firmly bond to each other and to the composite material block.

After sintering, the block is worked by extrusion molding, preferably it is hot-worked. Thereafter at least one partial strand is produced that has an upper face comprising composite material and an easy-to-solder or easy-to-weld lower face comprising base metal. Preferably two such partial strands are generated by dividing the strand formed by extrusion molding in the longitudinal direction thereof. It is, of course, possible to carry out additional longitudinal divisions perpendicular to the separating plane. The information that preferably two partial strands are produced should thus be interpreted to mean at least two. However, it is also possible to generate only one partial strand, by removing the base metal on one side of the strand formed by extrusion molding, for example by milling, so as to expose a surface comprising composite material.

After sintering, the base metal generally adheres with sufficient strength to the block, so that the block can be shaped allowing it to be inserted in an extrusion die with precise fit. For example, an approximately cylindrical block can be produced by pressing and subsequent sintering, the lateral area of which is subjected to a turning process before extrusion molding so as to achieve an adaptation to the dimensions of an extrusion die. The block is preferably worked by extrusion molding from a cylindrical shape into a shape having a rectangular cross-section.

The extrusion molding is preferably carried out at temperatures of at least 600° C., and more particularly between 700° C. and 950° C. This measure has the advantage that advantageously high compaction is achieved by the extrusion molding. Advantageously, it can be achieved in particular that the strand has a relative density of 99.9% of the theoretically possible density.

By dividing the strand formed by extrusion molding in the longitudinal direction, a semifinished product is obtained that has a layer comprising a silver-based composite material, which forms the upper face of the semifinished product for contact-making, and a carrier layer comprising an easy-to-solder or easy-to-weld base metal.

The two flanks of the strand extending from the contact-making upper face to the easy-to-solder and easy-to-weld lower face of the strand are preferably trimmed, notably by cutting or milling. In this way, it can be ensured that during further processing of the semifinished product, or during later use of an electrical contact produced with the semifinished product, no material of the carrier layer reaches the contact surface and impairs the function thereof. The flanks of the strand formed by extrusion molding can optionally be trimmed before or after the longitudinal division of the strand.

It is preferred to reduce the thickness of the strand generated by extrusion molding by way of rolling, notably by cold rolling. In this way, a strip-shaped semifinished product is particularly advantageous to produce. It is particularly preferred for the rolling to take place after longitudinally dividing the strand, which is to say, the partial strand is or the partial strands are rolled. It is further preferred for the thickness of the strand to be reduced during rolling by no more than 50% of the original thickness, so as to avoid that mechanical properties of the semifinished product are disadvantageously impaired. Notably when reducing the thickness by more than 50%, there is the risk that the material becomes too hard. It is particularly preferred for the thickness of the strand to be reduced during rolling by 30 to 50% of the original thickness.

According to an advantageous refinement of the invention, oxidation-protected metal powder is used for covering the composite material block, which is to say, the particles of the powder comprising the base metal with which the block made of the composite material is covered are protected from oxidation by an organic coating. In this way, the formation of interfering oxide layers, which hamper the sintering process, can be counteracted. The organic coating is preferably selected so that it volatizes without residue during sintering, for example by evaporating.

In the method preferably a composite material is used that is a silver-metal oxide composite material. The metal oxides used can be notably tin oxide and/or zinc oxide and/or indium oxide and/or cadmium oxide. It is also possible, for example, to use bismuth oxide or tungsten oxide. It is possible for the composite material used according to the invention to comprise a plurality of metal oxides. Likewise, it is possible for the composite material to contain only a single metal oxide. The metal oxide component of the composite material preferably primarily comprises tin oxide. As an alternative, or in addition to the metal oxides, the silver-based contact material that is used may also contain carbon, for example in the form of graphite.

The composite material block covered with base metal powder is preferably subjected to cold isostatic pressing. Cold isostatic pressing can be carried out without difficulty at room temperature. In general, the cold isostatic pressing can also be carried out at elevated temperatures, however it is preferred for the cold isostatic pressing to be carried out a temperature at which the base metal is at most insignificantly oxidized in the presence of atmospheric oxygen.

EMBODIMENTS

1. A cylindrical block comprising a silver-based contact material is produced by mixing silver powder and tin oxide powder, cold isostatic pressing, and subsequent sintering. This block, for example, may comprise 8 to 14 percent by weight of metal oxide, the remainder being silver.

The composite material block is wrapped with a foil made of nickel or a nickel iron alloy. The wrapped block is subsequently covered with oxidation-protected copper or brass powder and is then cold isostatically pressed.

The isostatically pressed block is sintered in a reducing atmosphere, for example under hydrogen, at a temperature of 700° C., for example for 30 minutes to 1 hour, and is subsequently sintered under nitrogen at 800° C. to 900° C., for example for 2 to 5 hours. The sintered block is subsequently subjected to a turning step, so that it can be inserted with precise fit in an extrusion press. Then the block is formed by extrusion molding at a temperature of 750° C. to 775° C. from the cylindrical shape thereof into a shape having a rectangular cross-section.

The flanks of the strand produced in this way are cut off and the strand is subsequently divided in the longitudinal direction. The partial strands formed in this way are subsequently cold-rolled, reducing the thickness thereof by 30 to 50%, for example by 45%. The strip-shaped semifinished product produced in this way comprises a carrier layer, the thickness of which constitutes approximately 10% to 20% of the thickness of the composite material layer, and can be used to produce electrical contact pieces by cutting sections off the semifinished product and forming them according to the requirements of a specific application.

2. A cylindrical block comprising a silver-based contact material is produced by mixing silver powder and graphite powder, by cold isostatic pressing, and subsequent sintering. This block, for example, may comprise 2 to 5 percent by weight of carbon, the remainder being silver. The composite material block is covered with powder made of copper or a copper-base alloy and sintered for several hours under a hydrogen atmosphere at 750° C. to 775° C. The sintered block can be further processed as described in the embodiment above.

The invention claimed is:

1. A method for producing a strand-shaped, semifinished product for electrical contacts, wherein the semifinished product has an upper face comprising a silver-based composite material intended for the electrical contact-making, one or more metal oxides or carbon being embedded in the composite material, and a carrier layer comprising easy-to-solder or easy-to-weld base metal, which carries the composite material, comprising the following steps:

producing a block from the silver-based composite material using a powder-metallurgical process;

covering the block comprising the composite material with a powder of the easy-to-solder or easy-to-weld base metal;

isostatically pressing the block covered with the metal powder so as to compact the metal powder;

sintering the pressed block in a reducing atmosphere or in an inert atmosphere or in a vacuum preventing the formation of a liquid eutectic from the silver of the composite material and from the base metal with which the block comprising the silver-based composite material is covered;

working the sintered block by extrusion molding; and generating a partial strand having an upper face comprising composite material and a lower face comprising base metal.

2. The method according to claim 1, wherein two partial strands are generated by dividing the strand formed by extrusion molding in a longitudinal direction thereof.

3. The method according to claim 1 wherein the composite material is a silver-metal oxide composite material.

4. The method according to claim 1 wherein the silver-based composite material contains at least one of the following oxides: tin oxide, zinc oxide, indium oxide, cadmium oxide.

5. The method according to claim 3 wherein sintering is carried out in a reducing atmosphere at a temperature of less than 700° C.

6. The method according to claim 5, wherein sintering takes place first in a reducing atmosphere at a temperature of less than 700° C., and subsequently sintering takes place in an inert atmosphere or under a vacuum at a higher temperature.

7. The method according to claim 1 wherein a powder comprising nickel, iron, copper or a copper-base alloy is used for covering the block comprising the silver-based composite material.

8. The method according to claim 7, wherein an alloy of copper with silver, or of copper with tin, or of copper with nickel is used as the copper-base alloy.

9. The method according to claim 1 wherein in that the particles of the metal powder are protected from oxidation by an organic coating.

10. The method according to claim 9, wherein the organic coating and the sintering conditions are selected so that the coating volatizes without residue during sintering.

11. The method according to claim 1, wherein the covered block is cold isostatically pressed.

12. The method according to claim 11, wherein the cold isostatic pressing is carried out at a temperature at which the base metal is at most insignificantly oxidized in the presence of atmospheric oxygen.

13. The method according to claim 1, wherein the extrusion molding is carried out at temperatures of at least 600° C.

14. The method according to claim 1, wherein the thickness of the strand generated by extrusion molding, or a partial strand, is reduced by rolling.

15. The method according to claim 1, wherein the strand comprises two flanks, where the two flanks of the strand extending from the contact-making upper face to the easy-to-solder and easy-to-weld lower face of the strand forming the carrier layer are trimmed.

16. The method according to claim 1, wherein an approximately cylindrical sintered block is produced, the lateral area of which is subjected to turning prior to extrusion molding.

17. The method according to claim 1, wherein the block is formed by extrusion molding from a cylindrical shape into a shape having a rectangular cross-section.

18. The method according to claim 1, wherein an intermediate layer acting as a diffusion barrier is provided between the composite material block and the cover formed of base metal powder.

19. The method according to claim 18, wherein the intermediate layer acting as the diffusion barrier is formed of iron, nickel or cobalt.

20. The method according to claim 18, wherein the intermediate layer acting as the diffusion barrier is dimensioned so that it is at least 3 µm thick in the finished semifinished product.

21. A method for producing a strand-shaped, semifinished product for electrical contacts, wherein the semifinished product has an upper face comprising a silver-based composite material intended for the electrical contact-making, one or more metal oxides or carbon being embedded in the composite material, and a carrier layer comprising easy-to-solder or easy-to-weld base metal, which carries the composite material, comprising the following steps:

producing a block from the silver-based composite material using a powder-metallurgical process;

covering the block comprising the composite material with a powder of the easy-to-solder or easy-to-weld base metal;

pressing the block covered with the metal powder so as to compact the metal powder;

sintering the pressed block in a reducing atmosphere or in an inert atmosphere or in a vacuum preventing the formation of a liquid eutectic from the silver of the composite material and from the base metal with which the block comprising the silver-based composite material is covered, wherein sintering is carried out in a reducing atmosphere at a temperature of less than 700° C.;

working the sintered block by extrusion molding; and generating a partial strand having an upper face comprising composite material and a lower face comprising base metal.

22. A method for producing a strand-shaped, semifinished product for electrical contacts, wherein the semifinished product has an upper face comprising a silver-based composite material intended for the electrical contact-making, one or more metal oxides or carbon being embedded in the composite material, and a carrier layer comprising easy-to-solder or easy-to-weld base metal, which carries the composite material, comprising the following steps:

producing a block from the silver-based composite material using a powder-metallurgical process;

covering the block comprising the composite material with a powder of the easy-to-solder or easy-to-weld base metal;

pressing the block covered with the metal powder so as to compact the metal powder;

sintering the pressed block in a reducing atmosphere or in an inert atmosphere or in a vacuum preventing the formation of a liquid eutectic from the silver of the composite material and from the base metal with which the block comprising the silver-based composite material is covered, wherein an approximately cylindrical sintered block is produced, the lateral area of which is subjected to turning prior to an extrusion molding;

working the sintered block by the extrusion molding; and generating a partial strand having an upper face comprising composite material and a lower face comprising base metal.

* * * * *